United States Patent
Lee et al.

(10) Patent No.: US 7,112,795 B2
(45) Date of Patent: Sep. 26, 2006

(54) METHOD OF CONTROLLING METALLIC LAYER ETCHING PROCESS AND REGENERATING ETCHANT FOR METALLIC LAYER ETCHING PROCESS BASED ON NEAR INFRARED SPECTROMETER

(75) Inventors: Ki-Beom Lee, Kuungki-Do (KR); Mi-Sun Park, Kyungki-Do (KR); Jong-Min Kim, Kyungki-Do (KR); Byung-Uk Kim, Kyungki-Do (KR); Chang-Il Oh, Kyungki-Do (KR)

(73) Assignee: Dong Jin Semichem Co., Ltd., Incheon (KR)

( * ) Notice: Subject to any disclaimer, the term of this patent is extended or adjusted under 35 U.S.C. 154(b) by 44 days.

(21) Appl. No.: 10/276,703

(22) PCT Filed: Mar. 27, 2001

(86) PCT No.: PCT/KR01/00488

§ 371 (c)(1),
(2), (4) Date: Nov. 18, 2002

(87) PCT Pub. No.: WO02/054155

PCT Pub. Date: Jul. 11, 2002

(65) Prior Publication Data
US 2003/0235997 A1   Dec. 25, 2003

(30) Foreign Application Priority Data
Dec. 30, 2000   (KR) .................... 10-2000-0087141

(51) Int. Cl.
*G01J 5/02*   (2006.01)
(52) U.S. Cl. ................... 250/339.07; 438/710

(58) Field of Classification Search ........... 250/339.07, 250/288, 258, 339.12, 339.09; 438/710, 438/714, 585, 719; 156/345.24, 345.13, 156/626; 356/316, 36
See application file for complete search history.

(56) References Cited

U.S. PATENT DOCUMENTS

| | | | |
|---|---|---|---|
| 4,633,804 A * | 1/1987 | Arii | 118/52 |
| 4,872,944 A * | 10/1989 | Rufin et al. | 438/14 |
| 5,282,925 A * | 2/1994 | Jeng et al. | 216/59 |
| 5,288,367 A | 2/1994 | Angell et al. | |
| 5,862,060 A | 1/1999 | Murray, Jr. | |
| 6,519,031 B1 * | 2/2003 | Gilton et al. | 356/316 |
| 6,707,038 B1 * | 3/2004 | Ellson et al. | 250/288 |
| 6,734,088 B1 * | 5/2004 | Purdy et al. | 438/585 |
| 6,743,733 B1 * | 6/2004 | Kitsunai et al. | 438/710 |

(Continued)

FOREIGN PATENT DOCUMENTS

JP   63-38268   2/1988

(Continued)

*Primary Examiner*—Otilia Gabor
(74) *Attorney, Agent, or Firm*—Staas & Halsey LLP

(57) ABSTRACT

In a method of controlling a metallic layer etching process for fabricating a semiconductor device or a liquid crystal display device, the composition of the etchant used in etching the metallic layer is first analyzed with the NIR spectrometer. The state of the etchant is then determined by comparing the analyzed composition with the reference composition. In case the life span of the etchant comes to an end, the etchant is replaced with a new etchant. By contrast, in case the life span of the etchant is left over, the etchant is delivered to the next metallic layer etching process. This analysis technique may be applied to the etchant regenerating process in a similar way.

7 Claims, 4 Drawing Sheets

U.S. PATENT DOCUMENTS

| | | |
|---|---|---|
| 6,749,715 B1 * | 6/2004 | Gilton et al. .......... 156/345.13 |
| 6,942,811 B1 * | 9/2005 | Patel et al. ..................... 216/2 |
| 2002/0121502 A1* | 9/2002 | Patel et al. ................... 216/73 |
| 2002/0195423 A1* | 12/2002 | Patel et al. ................... 216/73 |
| 2004/0040658 A1* | 3/2004 | Usui et al. ............. 156/345.24 |
| 2005/0082482 A1* | 4/2005 | Ludviksson ................ 250/342 |

FOREIGN PATENT DOCUMENTS

| | | |
|---|---|---|
| JP | 09-191007 | 7/1997 |
| JP | 9-235926 | 9/1997 |
| JP | 10335309 A * | 12/1998 |
| KR | 2000-8553 | 2/2000 |

\* cited by examiner calibration:Al-Etchant NEW(CH3COOH)   Property:CH3COOH

METHOD OF CONTROLLING METALLIC LAYER ETCHING PROCESS AND REGENERATING ETCHANT FOR METALLIC LAYER ETCHING PROCESS BASED ON NEAR INFRARED SPECTROMETER

BACKGROUND OF THE INVENTION (a) Field of the Invention

The present invention relates to a method of controlling a metallic layer etching process and a method of regenerating an etchant for the metallic layer etching process based on a near infrared (NIR) spectrometer and, more particularly, to an NIR spectrometer-based etching control method and etchant regeneration method which automatically analyzes the composition of an etchant used in the lithography process for fabricating a semiconductor device or a liquid crystal display device in real time, thereby controlling the etching process and regenerating the etchant in an accurate and effective manner while reducing the required period of time therefor.

(b) Description of the Related Art

As a large-size semiconductor device or liquid crystal display device becomes to be the choice of electronic consumers, the amount of solvents used in fabricating such a device has been significantly increased. In this situation, effective use of the solvents should be made to optimize the device fabrication process. Among such solvents, etchant is used to etch a metallic layer of chrome or aluminum, on which a photoresist layer of a predetermined pattern is formed as a mask, so that a patterned metallic layer is formed. After the etching is made, the etchant is recovered, and re-used in the next etching process. As the etchant is repeatedly used, alien materials are continuously incorporated into the etchant, and the initial composition of the etchant is continuously altered. When such an alteration degree in the initial composition exceeds the critical value, the etchant cannot be used for the etching purpose without adjusting the composition. In this case, the alien materials should be removed from the etchant, and the components of the etchant exhausted through the etching process should be newly supplied thereto. That is, the etchant should be regenerated before it is reused in the next etching process.

Meanwhile, a conventional way of determining whether the etchant can be still used for the etching purpose is to observe whether spots or stains are formed on a substrate during the etching process, thereby identifying the degree of contamination and variation in the composition of the etchant. However, with such a technique, the etchant cannot be analyzed quantitatively and suitably. That is, either the etchant to be waste-disposed may be used for the etching while causing process failure, or the etchant to be reused may be waste-disposed.

In the regeneration process of the etchant, the components of the etchant should be analyzed from time to time to regenerate the etchant of a uniform composition. For this purpose, conventionally, the user himself extracts a sample from the regenerator, and analyzes the sample with various analytical instruments. However, this method needs much time and effort for the analysis. Furthermore, when the required components determined by the time-consuming analysis are supplied to the regenerator, the regenerator is liable to be full of the etchant due to the etchant delivered from the etching process. In this case, part of the etchant should be discharged from the regenerator to supply the required components thereto. Consequently, the operation of the regenerator is discontinuously made, resulting in increased production cost and time.

Furthermore, in order to analyze various components of the etchant, separate analytic instrument should be used for each component, and the concentration of the sample should be adjusted to be suitable for each analytic instrument, and more than thirty minutes is required for the analysis. This makes it difficult to perform the desired real-time analysis.

In order to overcome such problems, it has been recently proposed that an on-line analytic equipment should be used for such an etchant analysis. However, the currently available on-line analytic equipment at best makes automatic sampling so that the desired real-time etchant analysis cannot be achieved. Furthermore, with the currently available on-line analytic equipment, collective information for treating and processing the etchant used in the lithography process cannot be obtained in real time. Therefore, there is a demand for a technique where the composition of the etchant can be analyzed in real time, and the etchant should be appropriately treated on the basis of the analysis.

SUMMARY OF THE INVENTION

It is an object of the present invention to provide a method of controlling a metallic layer etching process which can detect variation in the composition of the etchant and concentration of metallic impurities in the etchant in real time during the process of fabricating a semiconductor device or a liquid crystal display device to manage the life span of the etchant.

It is another object of the present invention to provide a method of controlling a metallic layer etching process which can provide a standard value for the regeneration time or the waste-disposal time of the etchant to improve efficiency in use of the etchant while reducing device production cost.

It is still another object of the present invention to provide a method of regenerating an etchant which can analyze composition of the etchant in real time, and control the amount and ratio of the raw materials to be supplied to a regenerator, thereby obtaining the desired etchant having a suitable and uniform composition.

It is still another object of the present invention to provide a method of controlling a metallic layer etching process and a method of regenerating an etchant, which can simultaneously analyze various components of the etchant for a short period of time during the process of fabricating a semiconductor device or a liquid crystal display device, resulting in enhanced analytic efficiency, rapid processing, and improved quality control.

These and other objects may be achieved by a method of controlling a metallic layer etching process and a method of regenerating an etchant for the metallic layer etching process based on a near infrared (NIR) spectrometer.

In the metallic layer etching process controlling method, the composition of the etchant are first analyzed using the NIR spectrometer. The life span of the etchant is then identified by comparing the analyzed composition with reference composition. In case the life span of the etchant comes to an end, the etchant is replaced with a new etchant. By contrast, in case the life span of the etchant is left over, the etchant is reused in the next metallic layer etching process.

In the etchant regenerating process, the composition of the etchant in a regenerator for adjusting the composition of the etchant, are first analyzed with the NIR spectrometer. The components to be newly supplied are then identified through comparing the analyzed composition with reference composition. The required components are supplied into the regenerator.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or the similar components, wherein.

DETAILED DESCRIPTION OF THE PREFERRED EMBODIMENTS

Figure 1:
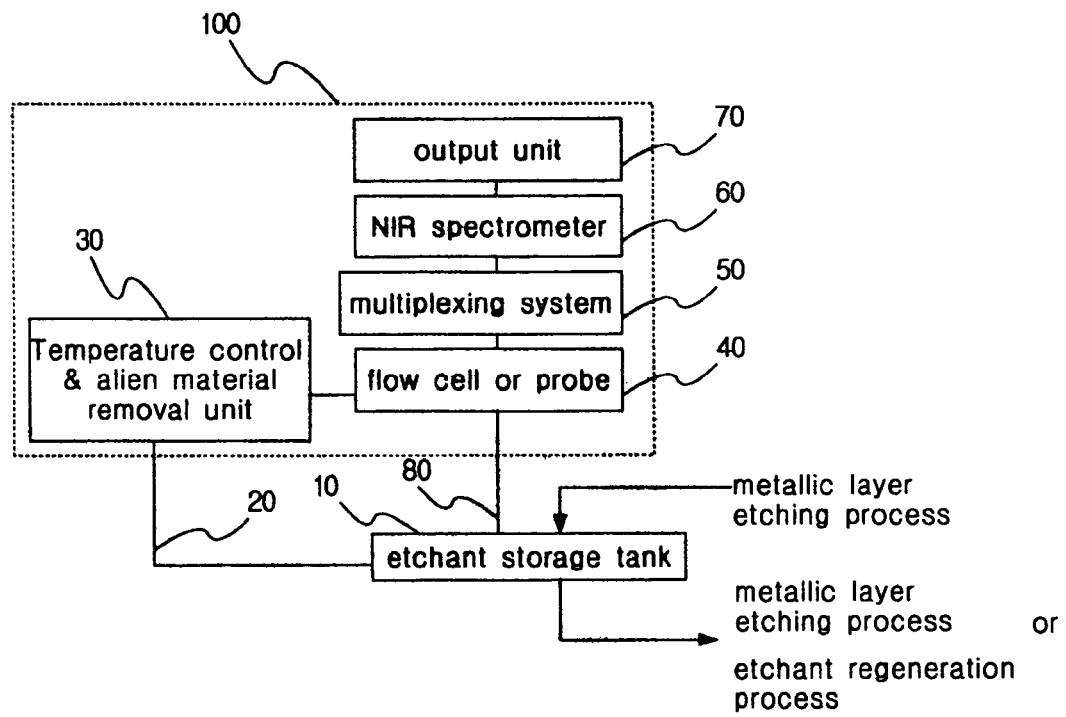
FIG. 1 is a block diagram showing the system for controlling a metallic layer etching process utilizing a NIR spectrometer according to a preferred embodiment of the present invention.

Preferred embodiments of this invention will be explained with reference to the accompanying drawings.

In the process of fabricating a semiconductor device or liquid crystal display device, an etchant is sprayed onto a substrate sequentially overlaid with a metallic layer and a patterned photoresist so that the metallic layer is etched through the photoresist pattern. Thereafter, the photoresist is removed while leaving the desired pattern at the metallic layer. At this time, the etchant containing the etched metallic residues is collected in an etchant collection tank placed below the substrate. When the amount of etchant in the collection tank reaches a predetermined value, it is delivered to an etchant storage tank by a delivering pump. Since each component of the etchant has its characteristic light absorption wavelength, the composition of the etchant can be analyzed in real time by detecting the light absorption of the etchant at near infrared (NIR) wavelength range with a NIR spectrometer.

The NIR spectrometer-based analysis technique is one of real-time analysis techniques recently developed. In the latter half of the nineteen-seventies, a technique of measuring moisture and protein contents in the wheat with the NIR spectrometer was officially recognized in Canada and U.S.A. Since then, the NIR spectrometer has been used in the fields of fine chemistry, pharmacy, or petrochemical plant operation automation. For instance, there are various techniques such as a technique of controlling yield of olefin in olefin polymerization through analyzing hydrocarbons contents in the olefin with NIR spectrometer (Japanese Patent Laid-open Publication No. Hei2-28293), a technique of measuring components of grain in real time (U.S. Pat. No. 5,751,421), a technique of measuring the amount of isomers of hydrocarbons in real time (U.S. Pat. No. 5,717,209), and a technique of analyzing the amount of aromatic compounds in hydrocarbons in real time (U.S. Pat. No. 5,145,785).

The NIR ray used in the NIR spectrometer is a light having wavelength of about 700–2500 nm, preferably having frequency of 4,000–12,000 $cm^{-1}$ (about 830–2500 nm), which is an intermediate range between the visible ray of 12,000–25,000 $cm^{-1}$, and the middle infrared ray of 400–4,000 $cm^{-1}$. Thus, the NIR ray is lower in energy than the visible ray, but higher than the middle-infrared ray. The energy of the NIR ray is correspond to the energy of a combination band and an overtone band of molecular vibrational energies of functional groups such as —CH, —OH, and —NH. As the absorption of the NIR ray by the combination band and the overtone band is significantly weak, variation in the NIR ray absorption according to the change of the absorption intensity is smaller than that of the middle infrared absorption spectrum by $1/10$–$1/1000$. Therefore, under the application of the NIR ray, the composition of the sample can be directly analyzed without diluting. Furthermore, due to the overlapping of a plurality of overtone bands and combination bands, and light absorption by hydrogen bonding or molecular interaction, quantitative analysis with respect to various components of the sample can be performed simultaneously. For the quantitative analysis of a multiple-components sample, the ray of NIR wavelengths, which are characteristic to the multiple-components, is radiated to the sample. Then the absorption peaks are monitored, and the concentrations of each component are derived with reference to a standard calibration curve showing the relation of concentration and light absorption of the component. In case the light absorption peaks of the respective components are overlapped, multiple regression analysis can be carried out to analyze the effect of each component. Accordingly, the analysis based on the NIR spectrometer can be rapidly carried out in 1 minute or less even if several components are analyzed simultaneously.

In order to analyze the composition of the etchant in real time with the NIR spectrometer, various techniques can be used. For instance, NIR ray absorption of the sample can be measured by dipping a detection probe into an etchant storage tank or into a sample from the etchant storage tank, and by detecting the light absorption of the sample. Alternatively, NIR ray absorption of the sample can be measured by flowing the etchant sample to a flow cell, and by detecting the light absorption of the flow cell.

In the technique of using the detection probe, the probe having an optical fiber cable is dipped into the etchant, and the light absorption, which are characteristic to the respective component of the etchant, are analyzed. Thereby, variations of the composition of the etchant, and variations of the concentrations of the metallic residues dissolved in the etchant are detected. Since, the probe has an NIR radiation and detection parts, the probe can measure light absorption of the components at their characteristic wavelengths in real time.

In the technique of using the flow cell, the flow cell has a sampling port which is formed on a regenerator or an etchant storage tank for sampling the etchant therefrom, and the light absorption of the etchant sample is analyzed by the NIR spectrometer, thereby detecting the composition of the etchant. In the present invention, in order to analyze the composition of the etchant in real time with the NIR spectrometer, the two techniques can be selectively used to the etching process of the semiconductor device and liquid crystal display device according to the temperature of the etchant, the amount of alien materials therein etc, FIG. 1 is a block diagram showing an example of the system for controlling a metallic layer etching process utilizing a NIR spectrometer. The controlling system includes an analysis system 100, which includes a temperature control and alien material removal unit 30, a flow cell or probe 40, a multiplexing system 50, an NIR spectrometer 60 having an NIR radiation lamp, a monochromator and a detector, and an output unit 70. A tungsten-halogen lamp may be used for the NIR radiation lamp, an AOTS(acousto-optical tunable scanning), FT(Fourier transform) or a grating for the monochromator, and an indium gallium arsenic (InGaAs) or PbS detector for the detector.

In operation, an etchant sample is delivered from the storage tank 10 to the temperature control and alien material removal unit 30 via a fast loop 20. The temperature control and alien material removal unit 30 controls the sample to be at ambient temperature, and removes alien materials from the sample. Then, the sample is delivered to the flow cell or probe 40 to perform the NIR absorption analysis. Since the NIR spectrometer 60 produces different analysis results according to the temperature of the sample, the temperature of the sample should be adjusted to the same temperature with a standard sample, which is used to make a calibration curve showing the relation of concentration and absorbance. The NIR spectrometer 60 measures the absorption spectra of the sample in the flow cell or probe 40 with its NIR radiation lamp, the monochromator, and the detector. The analysis results are output by way of the output unit 70. The sample used for the analysis is delivered to the etchant storage tank 10 through a recovery system 80. As shown in FIG. 1, a multiplexing system 50 is preferably provided to change the flow cell or probe 40 analyzed by the spectrometer 60 in case one NIR spectrometer 60 is used to analyze several samples from multiple process lines. In this case, the analysis system 100 is provided with plural numbers of fast loops 20 and flow cells or probes 40 connected to the respective process lines, therefore, the samples from the multiple process lines can be analyzed with one spectrometer 60.

In order to quantitatively analyze the composition of the etchant and the metallic contents dissolved therein, a calibration curve showing the relation of concentration and absorbance of each component should be previously made. The calibration curve is made through measuring the light absorbance of a component of a standard etchant sample while varying the concentration of the component. Then the concentration of a component in a sample can be determined by comparing the detected absorbance with the absorbance of the calibration curve, thereby identifying the composition of the sample. The analyzed composition is compared with the reference composition to determine whether the etchant should be regenerated or reused, in other word, whether the etchant is usable.

In case the amount of each component of the etchant and the metallic contents dissolved therein does not exceed the reference value, that is, in case the life span of the etchant does not come to an end, a separate delivering pump is operated to deliver the etchant to the next metallic layer etching process. By contrast, in case the life span of the present etchant comes to an end, a new etchant is introduced into the subsequent metallic layer etching process, and the present etchant is delivered to a regenerator for regeneration of the etchant, or waste-disposed.

In this way, the composition of the etchant is automatically analyzed with a predetermined time interval using an on-line NIR spectrometer synchronized with the process lines so that the historical recording with respect to the composition of the etchant can be established, and the state of the etchant in the etching process can be quantitatively determined. This makes it possible to use the etchant in accurate and effective manners.

Figure 2:
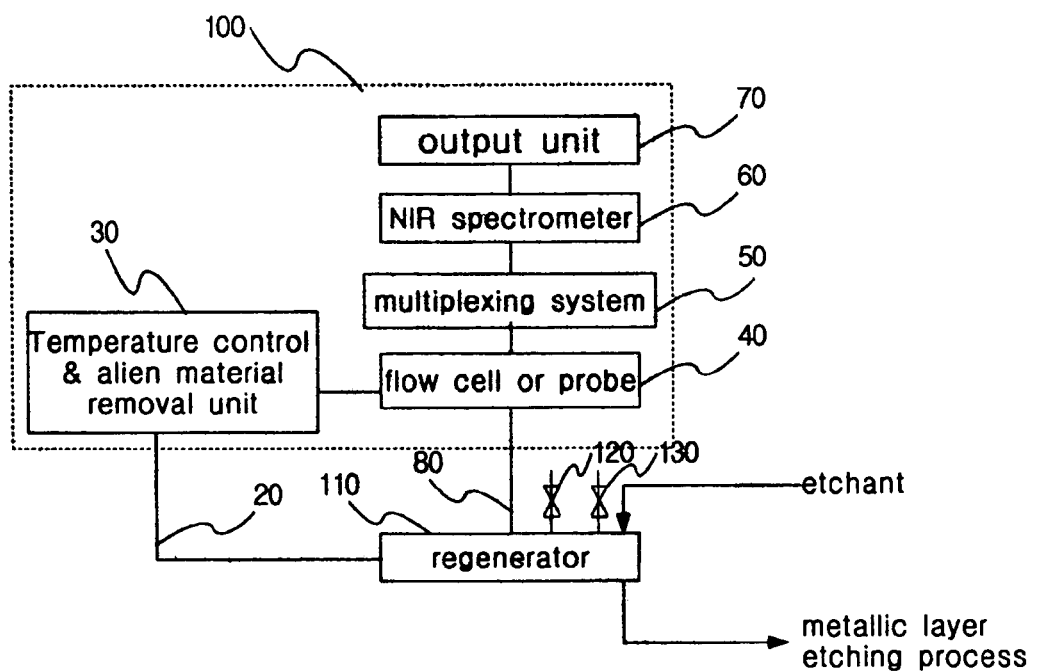
FIG. 2 is a block diagram showing the system for regenerating the etchant utilizing a NIR spectrometer according to a preferred embodiment of the present invention.

A method of regenerating the etchant using a NIR spectrometer will be now explained with reference to FIG. 2. FIG. 2 is a block diagram showing the system for regenerating the etchant utilizing a NIR spectrometer. The regeneration system includes the same analysis system 100 used in the metallic layer etching process control system.

The method of regenerating the etchant using the NIR spectrometer utilizes the same principle as in the metallic layer etching process control method. The composition of the etchant in a regenerator 110 is analyzed in real time with the analysis system 100 including the NIR spectrometer 60. It is preferable that the wavelength range of the NIR spectrometer for analyzing the composition is 700–2500 nm. The analyzed compositions of the etchant are compared with the reference composition, and the components to be newly supplied are identified from the comparison. In accordance with the identification results, valves 120 and 130 are opening to supply the required components to the regenerator 110. The regenerator 110 may be operated under low pressure, high pressure, or middle pressure. In this way, the etchant is regenerated upon receipt of the required components such that it has the same composition as the initial etchant. The regenerated etchant is again fed to the metallic layer etching process.

The analysis system 100 can be connected to a controller (not shown), and the controller controls the valves 120 and 130 such that they automatically supply the required constituents according to the analysis result. In the metallic layer etching process, the process automation can be also applied in the same manner. The components of the etchant that can be analyzed with the NIR spectrometer include hydrochloric acid(HCl), nitric acid($HNO_3$), acetic acid ($CH_3COOH$), phosphoric acid($H_3PO_4$), fluoric acid(HF), oxalic acid($(COOH)_2$), sulfuric acid($H_2SO_4$), cerium ammonium nitrate(CAN), and water, but not limited thereto.

The following examples are provided just to illustrate the present invention in more detail. In the examples, the percentage and the mixture ratio represent weight percent and weight ratio.

EXAMPLE 1 to 3

Etchants having the composition (1) to (3) listed below were used in the metallic etching process control system shown in FIG. 1, and the composition of the etchant were analyzed in real time in the controlling system. The analysis was performed at various concentrations of the etchant components. The results of the analysis are compared with the analysis results obtained from the conventional analysis method, which uses various analysis instruments. Namely, in order to evaluate the adequacy of the NIR spectrometer-based analysis for the etching process, the etchant analysis results from the NIR spectrometer were compared with the etchant analysis results from the conventional analysis system over the long time period of seven months. The comparison results are listed in Table 1.

(1) hydrochloric acid, nitric acid, and water
(2) nitric acid, acetic acid, phosphoric acid, and water
(3) cerium ammonium nitrate, nitric acid, and water

TABLE 1

| Component | Acetic acid | Phosphoric acid | Nitric acid | Water |
|---|---|---|---|---|
| Measurement range | 5–35 wt % | 30–70 wt % | 3–30 wt % | 5–30 wt % |
| Correlation coefficient ($R^2$) | 0.9999 | 0.9998 | 0.9990 | 0.9999 |
| Standard deviation (SD) | 0.050 | 0.094 | 0.174 | 0.023 |

As known from Table 1, the correlation coefficient in measurement of the present NIR analysis system to the conventional analysis system was appeared to reach 0.9999, and the standard deviation to be at maximum about 0.17. That is, the present system and the conventional system produce substantially the same analysis results.

Figure 3:
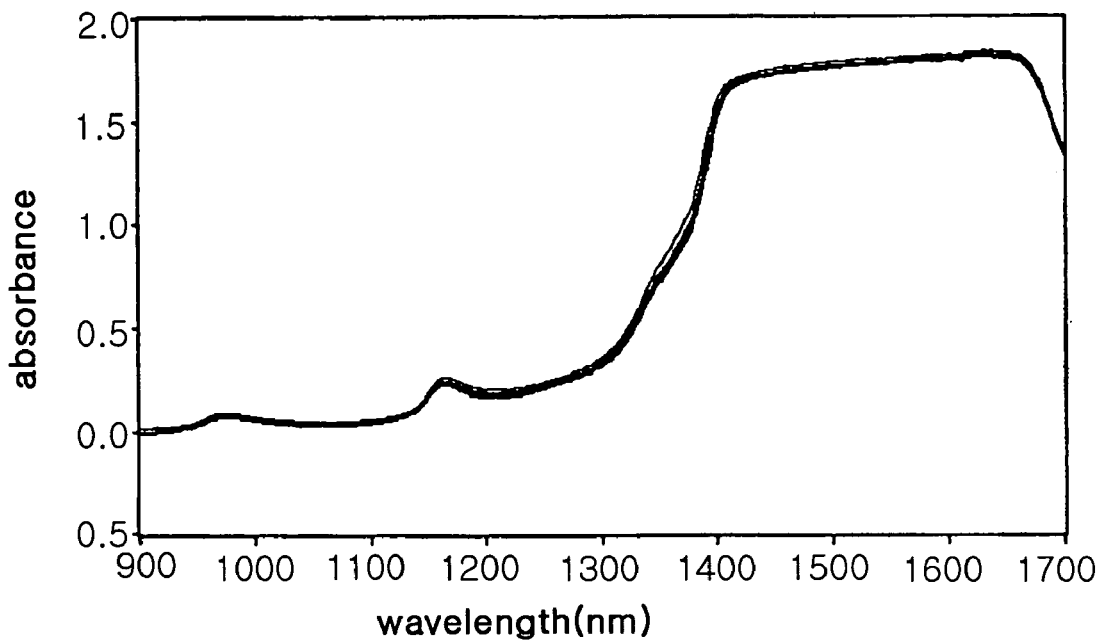
FIG. 3 is a graph for showing an example of the light absorption spectrum of an etchant in the wavelength region of 900–1700 nm measured by the NIR spectrometer.
Figure 4:
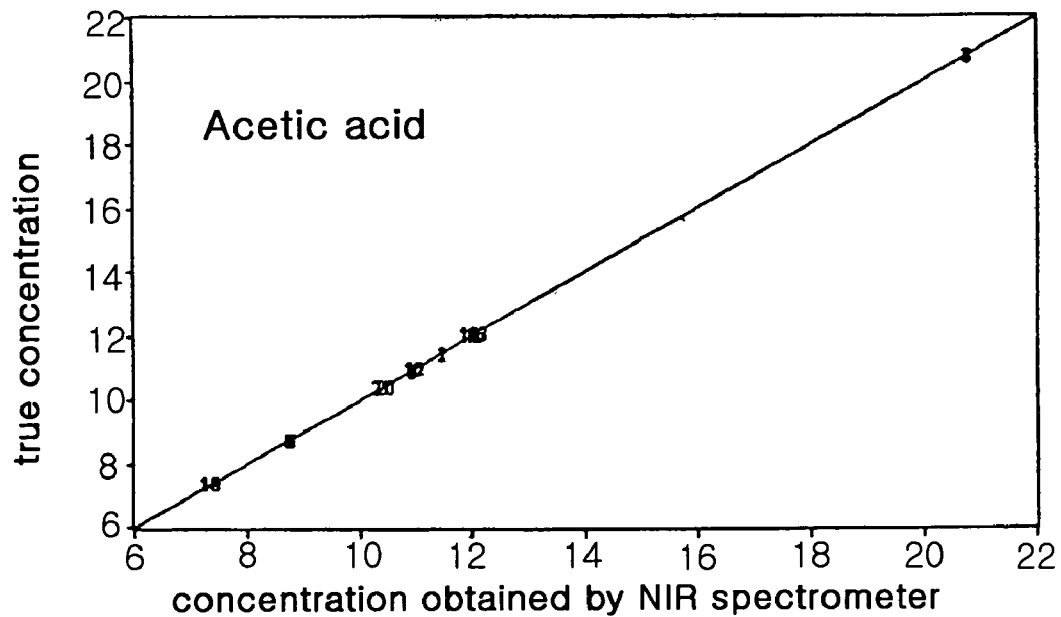
FIG. 4 is a graph showing the relation of the true concentration of acetic acid in an etchant and the concentration of the same obtained by the NIR spectrometer.
Figure 5:
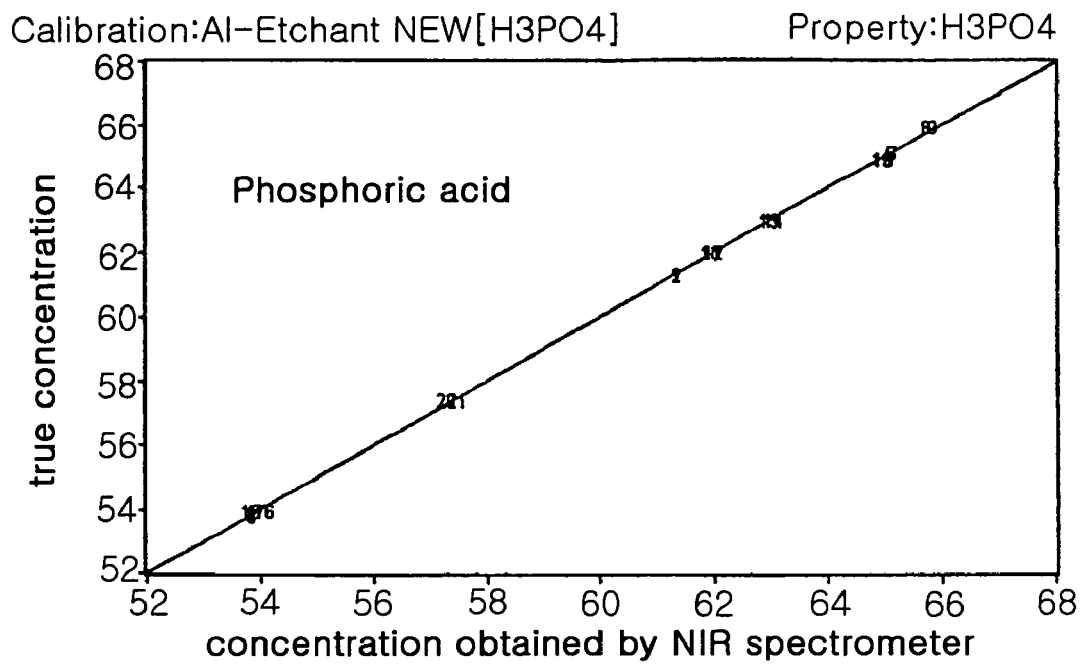
FIG. 5 is a graph showing the relation of the true concentration of phosphoric acid in an etchant and the concentration of the same obtained by the NIR spectrometer.
Figure 6:
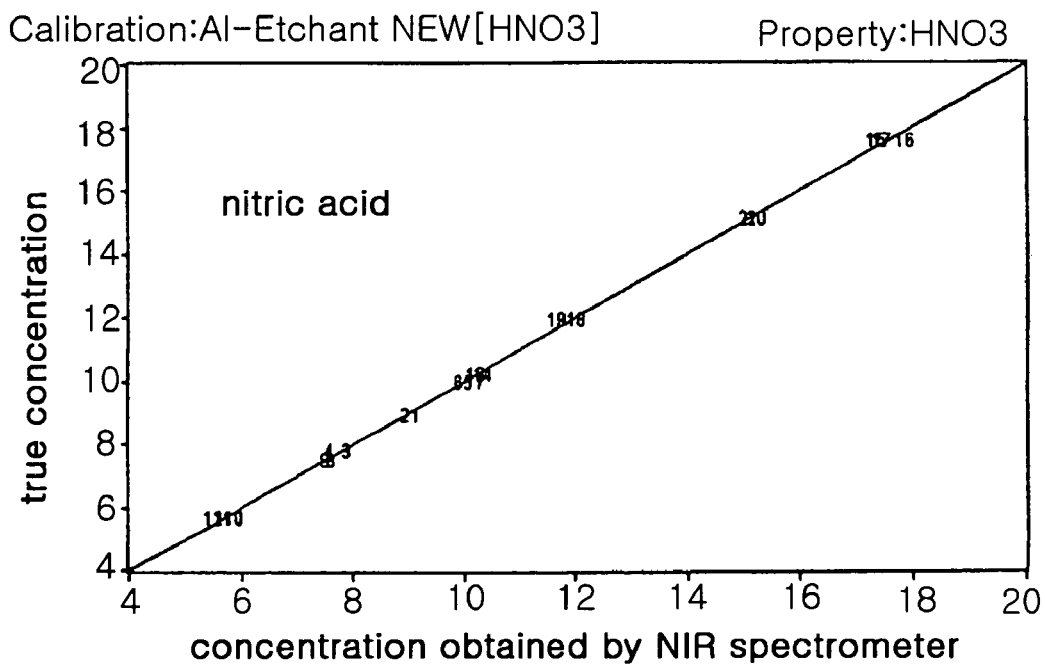
FIG. 6 is a graph showing the relation of the true concentration of nitric acid in an etchant and the concentration of the same obtained by the NIR spectrometer.
Figure 7:
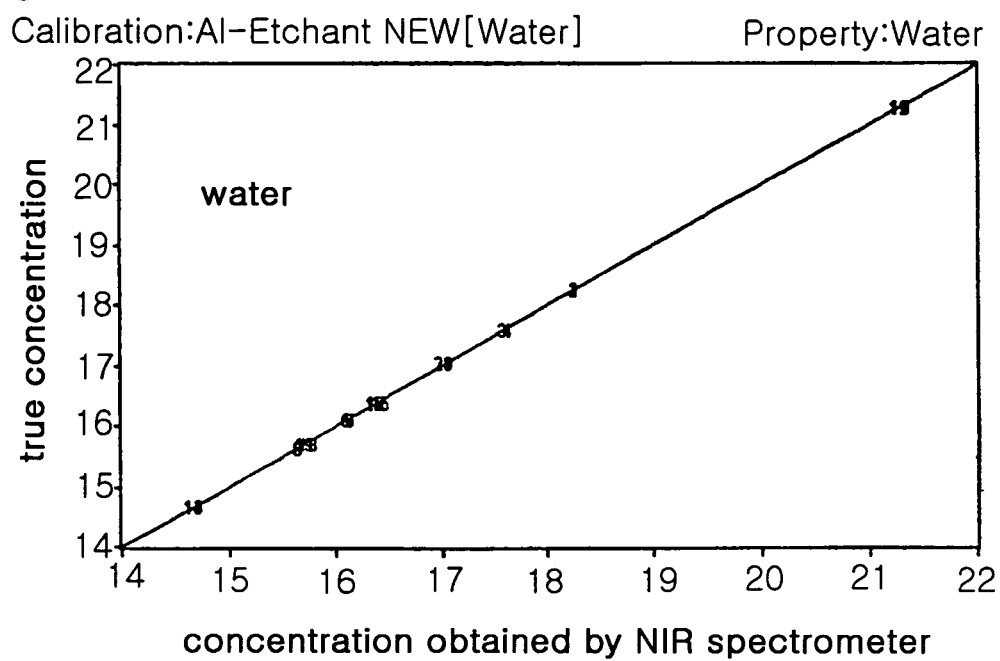
FIG. 7 is a graph showing the relation of the true concentration of water in an etchant and the concentration of the same obtained by the NIR spectrometer.

FIG. 3 is a graph for showing an example of the light absorption spectrum of the etchant (1) in the wavelength range of 900–1700 nm. FIGS. 4 to 7 are graphs showing the true concentrations of etchant components (acetic acid, phosphoric acid, nitric acid, and water) and the concentrations obtained through the NIR spectrometer. As known from the graphs, the concentrations obtained by the NIR spectrometer have good correlation with respect to the true concentration determined by conventional analytical instrument.

As described above, the inventive method of controlling a metallic layer etching process and regenerating the etchant for the etching process based on an NIR spectrometer makes it possible to accurately analyze the composition of the etchant used in the metallic layer etching process for fabricating a semiconductor device or a liquid crystal display device. Accordingly, the state of the etchant in the process is quantitatively analyzed so that the metallic layer etching process can be controlled in an effective manner. Furthermore, with the inventive method, the etchant used in the metallic layer etching process is regenerated in a reliable manner while reducing the amount of consumption of raw materials. In addition, it can be discriminated in real time whether the etchant is still usable in the process line, and this makes it possible to significantly enhance process yield.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A method of controlling a metallic layer etching process, the method comprising:
   removing alien material from a sample of an etchant;
   monitoring, in real time, at a predetermined temperature, absorption peaks of the etchant used for etching a metallic layer in the process of fabricating a semiconductor device or a liquid crystal display device with a near infrared spectrometer, wherein the near infrared spectrometer comprises a light source radiating a ray of wavelength range of 700–2500 nm;
   determining whether a concentration of each component of the etchant exceeds a corresponding reference value based on a standard calibration curve of a reference composition showing a relation of concentration and light absorption of each component to determine whether the etchant is usable; and
   either replacing the etchant with a new etchant in case the etchant is not usable, or using the etchant in a next metallic layer etching process in case the etchant is usable,
   wherein the etchant includes one or more materials selected from the group consisting of hydrochloric acid, nitric acid, phosphoric acid, fluoric acid, sulfuric acid, cerium ammonium nitride, and water.

2. The method of claim 1 wherein the near infrared spectrometer comprises at least one probe, the probe being dipped into an etchant storage tank to detect the light absorbance of the etchant.

3. The method of claim 1 wherein the near infrared spectrometer measures the light absorption of at least one flow cell containing the etchant delivered from an etchant storage tank.

4. The method of claim 1 wherein the step of either replacing the etchant with a new etchant or using the etchant in the next metallic layer etching process is performed automatically by a controller.

5. A method of regenerating an etchant, the method comprising:
   removing alien material from a sample of the etchant;
   monitoring, in real time, absorption peaks of the etchant by determining whether concentration of each component of the etchant exceeds a corresponding reference value based on a standard calibration curve of a reference composition showing a relation of concentration and light absorption of each component at a predetermined temperature in a regenerator for adjusting the composition of the etchant with a near infrared spectrometer, wherein the near infrared spectrometer comprises a light source radiating a ray of wavelength range of 700–2500 nm;
   determining components to be newly supplied to the etchant by comparing the monitored absorption peaks with peaks of the standard calibration curve of the reference composition; and
   supplying the components into the regenerator,
   wherein the etchant includes one or more materials selected from the group consisting of hydrochloric acid, nitric acid, phosphoric acid, fluoric acid, sulfuric acid, cerium ammonium nitride, and water.

6. A method of controlling a metallic layer etching process, the method comprising:
   removing alien material from a sample of an etchant;
   monitoring, in real time, at a predetermined temperature, a absorption peaks of the etchant used for etching a metallic layer in the process of fabricating a semiconductor device or a liquid crystal display device with a near infrared spectrometer by determining whether concentration of each component of the etchant exceeds a corresponding reference value based on a standard calibration curve showing a relation of concentration and light absorption of each component, wherein the near infrared spectrometer comprises a light source radiating a ray of wavelength range of 700–2500 nm;
   automatically adjusting, where monitored absorption peaks vary by an amount greater than a predetermined amount from the corresponding reference value, the composition to conform with the reference composition,
   wherein the etchant includes one or more materials selected from the group consisting of hydrochloric acid, nitric acid, phosphoric acid, fluoric acid, sulfuric acid, cerium ammonium nitride, and water.

7. A real time method of controlling a metallic layer etching process, wherein a used etchant includes one or more materials selected from the group consisting of hydrochloric acid, nitric acid, phosphoric acid, fluoric acid, sulfuric acid, cerium ammonium nitride, and water, the method comprising:

removing alien material from a sample of the used etchant;

using near infrared spectroscopy in a wavelength range of 700–2500 nm to monitor absorption peaks of components of the sample;

determining if the used etchant is reusable by comparing the absorption peaks of the components of the sample with a standard calibration curve of a reference composition showing a relation of concentration and light absorption of each component; and automatically adding components to the used etchant, where the used etchant is determined to be reusable, to conform a composition of the used etchant with the reference composition.

* * * * *

UNITED STATES PATENT AND TRADEMARK OFFICE
CERTIFICATE OF CORRECTION

PATENT NO.         : 7,112,795 B2                                                Page 1 of 1
APPLICATION NO. : 10/276703
DATED              : September 26, 2006
INVENTOR(S)        : Ki-Beom Lee et al.

It is certified that error appears in the above-identified patent and that said Letters Patent is hereby corrected as shown below:

Column 8, Line 48, delete "a" before "absorption".

Column 8, Line 51, after "whether" insert --a--.

Column 8, Line 59, after "where" insert --the--.

Signed and Sealed this

Twentieth Day of February, 2007

JON W. DUDAS
*Director of the United States Patent and Trademark Office*